(12) United States Patent
Goldfarb et al.

(10) Patent No.: US 8,303,608 B2
(45) Date of Patent: *Nov. 6, 2012

(54) FIXATION DEVICES FOR VARIATION IN ENGAGEMENT OF TISSUE

(75) Inventors: Eric A. Goldfarb, San Francisco, CA (US); Alfred H. Raschdorf, Kings Park, NY (US); Jaime E. Sarabia, San Jose, CA (US); Sylvia Wen-Chin Fan, Burlingame, CA (US); Kent D. Dell, Redwood City, CA (US); Jan Komtebedde, Los Gatos, CA (US); Ferolyn T. Powell, San Francisco, CA (US)

(73) Assignee: Evalve, Inc., Menlo Park, CA (US)

( * ) Notice: Subject to any disclaimer, the term of this patent is extended or adjusted under 35 U.S.C. 154(b) by 119 days.

This patent is subject to a terminal disclaimer.

(21) Appl. No.: 12/883,013

(22) Filed: Sep. 15, 2010

(65) Prior Publication Data

US 2011/0004227 A1 Jan. 6, 2011

Related U.S. Application Data

(63) Continuation of application No. 10/975,555, filed on Oct. 27, 2004, now Pat. No. 7,811,296, which is a continuation-in-part of application No. 10/803,444, filed on Mar. 17, 2004, now Pat. No. 7,563,273, which is a continuation of application No. 09/894,463, filed on Jun. 27, 2001, now Pat. No. 6,752,813, which is a continuation-in-part of application No. 09/544,930, filed on Apr. 7, 2000, now Pat. No. 6,629,534.

(60) Provisional application No. 60/128,690, filed on Apr. 9, 1999.

(51) Int. Cl.
*A61B 17/08* (2006.01)
(52) U.S. Cl. ...................................... 606/151
(58) Field of Classification Search .................. 606/221
See application file for complete search history.

(56) References Cited

U.S. PATENT DOCUMENTS

| 6,063,104 | A  | * | 5/2000 | Villar et al. | 606/213 |
| 6,544,273 | B1 | * | 4/2003 | Harari et al. | 606/151 |
| 7,357,805 | B2 | * | 4/2008 | Masuda et al. | 606/142 |
| 7,811,296 | B2 | * | 10/2010 | Goldfarb et al. | 606/151 |

* cited by examiner

*Primary Examiner* — Melanie Tyson
(74) *Attorney, Agent, or Firm* — Sughrue Mion, PLLC; Jonathan D. Feuchtwang

(57) ABSTRACT

Devices, systems and methods are provided for tissue approximation and repair at treatment sites, particularly in those procedures requiring minimally-invasive or endovascular access to remote tissue locations. Fixation devices are provided to fix tissue in approximation with the use of distal elements. In some embodiments, the fixation devices have at least two distal elements and an actuatable feature wherein actuation of the feature varies a dimension of the at least two distal elements. In other embodiments, the fixation devices have at least two pairs of distal elements wherein the pairs of distal elements are moveable to engage tissue between opposed pairs of distal elements. Systems are also provided having fixation devices and accessories.

15 Claims, 12 Drawing Sheets

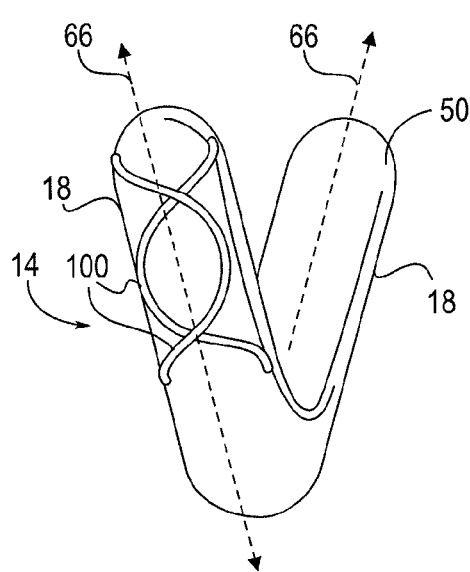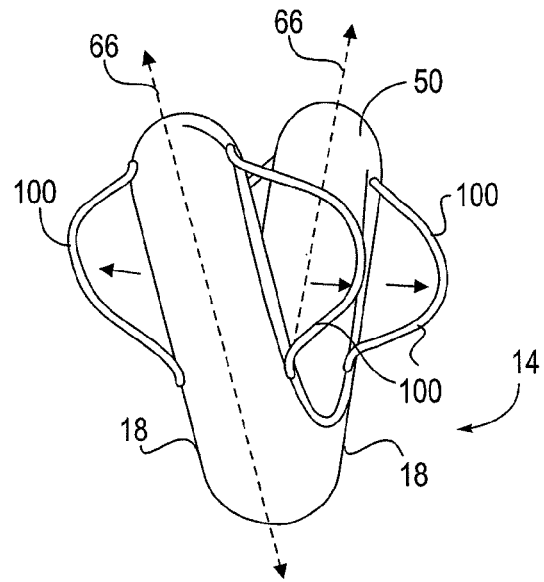
FIG. 8A  FIG. 8B
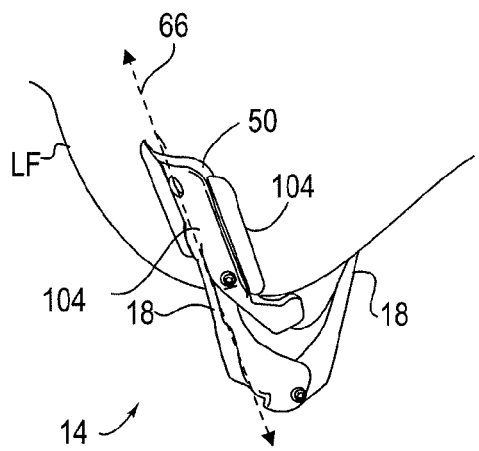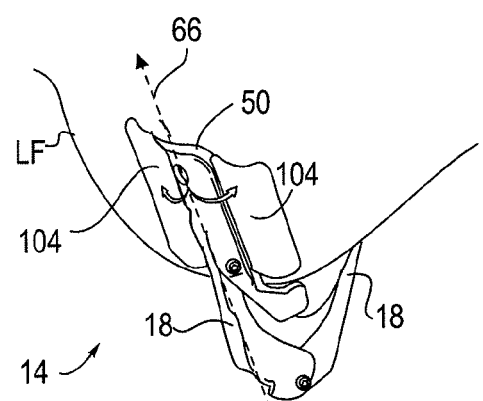
FIG. 9A  FIG. 9B

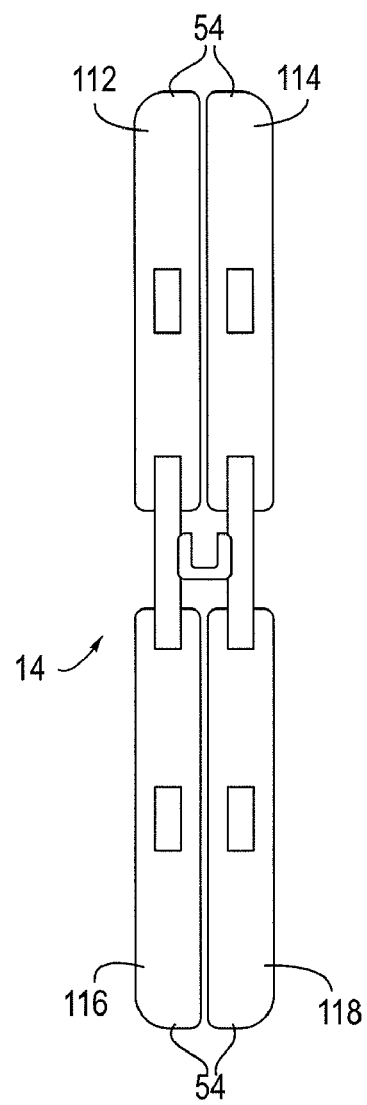
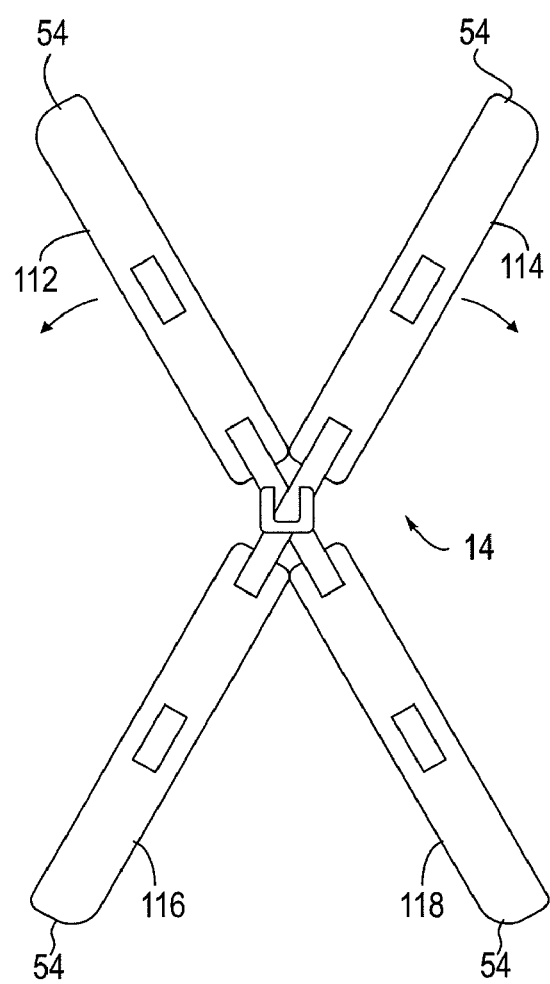
FIG. 12A
FIG. 12B

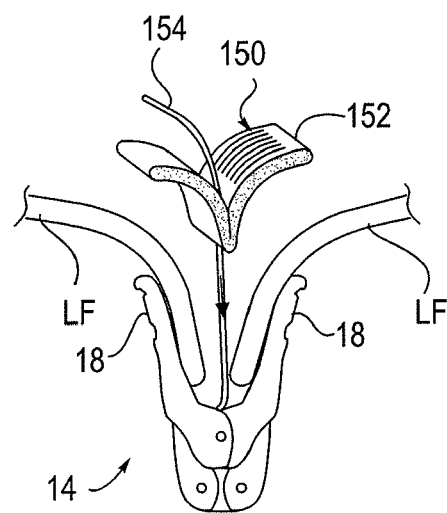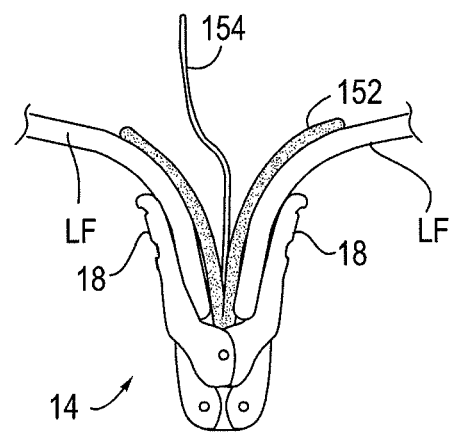
FIG. 17A  FIG. 17B
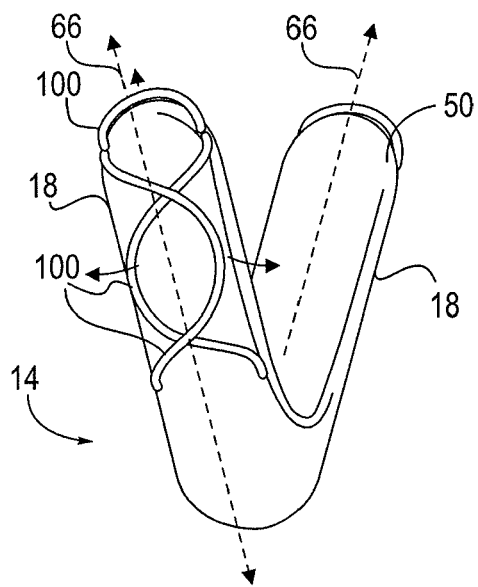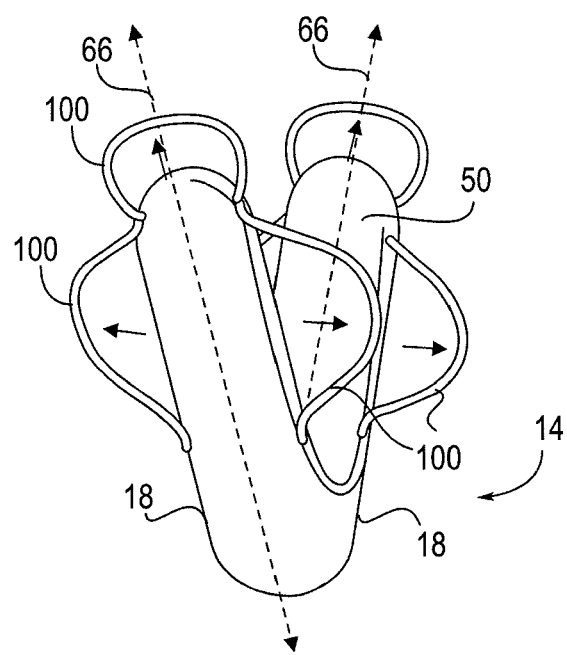
FIG. 18A  FIG. 18B

FIXATION DEVICES FOR VARIATION IN ENGAGEMENT OF TISSUE

CROSS-REFERENCES TO RELATED APPLICATIONS

The present application is a continuation of U.S. patent application Ser. No. 10/975,555 filed Oct. 27, 2004 (now U.S. Pat. No. 7,811,296), which is a continuation in part of U.S. patent application Ser. No. 10/803,444 filed Mar. 17, 2004 (now U.S. Pat. No. 7,563,273), which is a continuation of U.S. patent application Ser. No. 09/894,463 filed Jun. 27, 2001 (now U.S. Pat. No. 6,752,813), which is a continuation in part of U.S. patent application Ser. No. 09/544,930 filed Apr. 7, 2000 (now U.S. Pat. No. 6,629,534), and which is a non-provisional of, and claims the benefit of U.S. Provisional Patent Application No. 60/128,690, filed Apr. 9, 1999. The entire contents of each of the above listed patent applications is incorporated herein by reference.

BACKGROUND OF THE INVENTION

1. Field of the Invention

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to repair of valves of the heart and venous valves.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall may be damaged or otherwise dysfunctional. Commonly, the valve annulus may be damaged, dilated, or weakened limiting the ability of the mitral valve to close adequately against the high pressures of the left ventricle.

The most common treatments for mitral valve regurgitation rely on valve replacement or repair including leaflet and annulus remodeling, the latter generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

For these reasons, it would be desirable to provide alternative and additional methods, devices, and systems for performing the repair of mitral and other cardiac valves. Such methods, devices, and systems should preferably not require open chest access and be capable of being performed either endovascularly, i.e., using devices which are advanced to the heart from a point in the patient's vasculature remote from the heart or by a minimally invasive approach. Further, such devices and systems should provide features which allow repositioning and optional removal of a fixation device prior to fixation to ensure optimal placement. In addition, such devices and systems should provide features that assist in secure engagement of the targeted tissue (e.g. leaflet or other targeted structure) at the time of placement and over time (e.g. tissue in growth, maximal surface area of engagement). The methods, devices, and systems would also be useful for repair of tissues in the body other than heart valves. At least some of these objectives will be met by the inventions described hereinbelow.

2. Description of the Background Art

Minimally invasive and percutaneous techniques for coapting and modifying mitral valve leaflets to treat mitral valve regurgitation are described in PCT Publication Nos. WO 98/35638; WO 99/00059; WO 99/01377; and WO 00/03759.

Maisano et al. (1998) Eur. J. Cardiothorac. Surg. 13:240-246; Fucci et al. (1995) Eur. J. Cardiothorac. Surg. 9:621-627; and Umana et al. (1998) Ann. Thorac. Surg. 66:1640-1646, describe open surgical procedures for performing "edge-to-edge" or "bow-tie" mitral valve repair where edges of the opposed valve leaflets are sutured together to lessen regurgitation. Dec and Fuster (1994) N. Engl. J. Med. 331:1564-1575 and Alvarez et al. (1996) J. Thorac. Cardiovasc. Surg. 112:238-247 are review articles discussing the nature of and treatments for dilated cardiomyopathy.

Mitral valve annuloplasty is described in the following publications. Bach and Bolling (1996) Am. J. Cardiol. 78:966-969; Kameda et al. (1996) Ann. Thorac. Surg. 61:1829-1832; Bach and Bolling (1995) Am. Heart J. 129: 1165-1170; and Bolling et al. (1995) 109:676-683. Linear segmental annuloplasty for mitral valve repair is described in Ricchi et al. (1997) Ann. Thorac. Surg. 63:1805-1806. Tricuspid valve annuloplasty is described in McCarthy and Cosgrove (1997) Ann. Thorac. Surg. 64:267-268; Tager et al. (1998) Am. J. Cardiol. 81:1013-1016; and Abe et al. (1989) Ann. Thorac. Surg. 48:670-676.

Percutaneous transluminal cardiac repair procedures are described in Park et al. (1978) Circulation 58:600-608; Uchida et al. (1991) Am. Heart J. 121: 1221-1224; and Ali Khan et al. (1991) Cathet. Cardiovasc. Diagn. 23:257-262.

Endovascular cardiac valve replacement is described in U.S. Pat. Nos. 5,840,081; 5,411,552; 5,554,185; 5,332,402; 4,994,077; and 4,056,854. See also U.S. Pat. No. 3,671,979 which describes a catheter for temporary placement of an artificial heart valve.

Other percutaneous and endovascular cardiac repair procedures are described in U.S. Pat. Nos. 4,917,089; 4,484,579; and 3,874,338; and PCT Publication No. WO 91/01689.

Thoracoscopic and other minimally invasive heart valve repair and replacement procedures are described in U.S. Pat. Nos. 5,855,614; 5,829,447; 5,823,956; 5,797,960; 5,769,812; and 5,718,725.

BRIEF SUMMARY OF THE INVENTION

The invention provides devices, systems and methods for tissue approximation and repair at treatment sites. The devices, systems and methods of the invention will find use in a variety of therapeutic procedures, including endovascular, minimally-invasive, and open surgical procedures, and can be used in various anatomical regions, including the abdomen, thorax, cardiovascular system, heart, intestinal tract, stomach, urinary tract, bladder, lung, and other organs, vessels, and tissues. The invention is particularly useful in those procedures requiring minimally-invasive or endovascular access to remote tissue locations.

In some embodiments, the devices, systems and methods of the invention are adapted for fixation of tissue at a treatment site. Exemplary tissue fixation applications include cardiac valve repair, septal defect repair, vascular ligation and clamping, laceration repair and wound closure, but the invention may find use in a wide variety of tissue approximation and repair procedures. In a particularly preferred embodiment, the devices, systems and methods of the invention are adapted for repair of cardiac valves, and particularly the mitral valve, as a therapy for regurgitation. The invention enables two or more valve leaflets to be coapted using an "edge-to-edge" or "bow-tie" technique to reduce regurgitation, yet does not require open surgery through the chest and heart wall as in conventional approaches. In addition, the position of the leaflets may vary in diseased mitral valves depending upon the type and degree of disease, such as calcification, prolapse or flail. These types of diseases can result in one leaflet being more mobile than the other (e.g. more difficult to capture), and therefore more difficult to grasp symmetrically in the same grasp with the other leaflet. The features of the present invention allow the fixation devices to be adapted to meet the challenges of unpredictable target tissue geometry, as well as providing a more robust grasp on the tissue once it is captured.

Using the devices, systems and methods of the invention, the mitral valve can be accessed from a remote surgical or vascular access point and the two valve leaflets may be coapted using endovascular or minimally invasive approaches. While less preferred, in some circumstances the invention may also find application in open surgical approaches as well. According to the invention, the mitral valve may be approached either from the atrial side (antegrade approach) or the ventricular side (retrograde approach), and either through blood vessels or through the heart wall.

The fixation devices of the present invention each have a pair of distal elements (or fixation elements). In the main embodiments, each distal element has a first end, a free end opposite the first end, an engagement surface therebetween for engaging tissue and a longitudinal axis extending between the first and free end. The first ends of the at least two distal elements are movably coupled together such that the at least two distal elements are moveable to engage tissue with the engagement surfaces. Thus, the first ends are coupled together so that the distal elements can move between at least an open and closed position to engage tissue. Preferably, the engagement surfaces are spaced apart in the open position and are closer together and generally face toward each other in the closed position.

Each distal element has a width measured perpendicular to its longitudinal axis and a length measured along its longitudinal axis. In one embodiment suitable for mitral valve repair, the fixed width across engagement surfaces (which determines the width of tissue engaged) is at least about 2 mm, usually 3-10 mm, and preferably about 4-6mm. In some situations, a wider engagement is desired wherein the engagement surfaces have a larger fixed width, for example about 2 cm. The engagement surfaces are typically configured to engage a length of tissue of about 4-10 mm, and preferably about 6-8 mm along the longitudinal axis. However, the size of the engagement surfaces may be varied in width and/or length, as will be described in later sections.

The fixation device is preferably delivered to a target location in a patient's body by a delivery catheter having an elongated shaft, a proximal end and a distal end, the delivery catheter being configured to be positioned at the target location from a remote access point such as a vascular puncture or cut-down or a surgical penetration. In an alternative embodiment, the target location is a valve in the heart.

Optionally, the fixation devices of the invention will further include at least one proximal element (or gripping element). Each proximal element and distal element will be movable relative to each other and configured to capture tissue between the proximal element and the engagement surface of the distal element. Preferably, the distal elements and proximal elements are independently movable but in some embodiments may be movable with the same mechanism. The proximal element may be preferably biased toward the engagement surface of the fixation element to provide a compressive force against tissue captured therebetween.

In a first aspect of the present invention, fixation devices are provided that include at least two distal elements and an actuatable feature attached to at least one of the at least two distal elements. Actuation of the feature varies a dimension of at least one of the at least two distal elements which varies the size of its engagement surface. For example, in some embodiments, the actuatable feature is configured so that actuation varies the width of the distal element. In some of these embodiments, the actuatable feature comprises at least one loop which is extendable laterally outwardly in a direction perpendicular to the longitudinal axis. Thus, extension of the at least one loop increases the size of the engagement surface of the distal element, specifically the width. In others of these embodiments, the actuatable feature comprises at least one flap which is extendable laterally outwardly in a direction perpendicular to the longitudinal axis. And in still others, the actuatable feature comprises at least one pontoon which is expandable laterally outwardly in a direction perpendicular to the longitudinal axis. The pontoon may be expanded by inflation or any suitable means.

In some embodiments, the actuatable feature is configured so that actuation varies the length of the distal element. In some of these embodiments, the actuatable feature comprises at least one loop which is extendable laterally outwardly from its free end along its longitudinal axis. Thus, extension of the at least one loop increases the size of the engagement surface of the distal element, specifically the length. In others of these embodiments, each of the distal elements comprises an elongate arm and the actuatable feature comprises an extension arm coupled with the elongate arm. The extension arm is extendable from the elongate arm to increase the length of the distal element. For example, in some instances the extension arm is coupled with the elongate arm by a cam such that rotation of the cam advances the extension arm along the longitudinal axis. Extension or retraction of the extension arm may be actuated by movement of the fixation device. For example, when each distal element is moveable from a closed position (wherein the engagement surfaces of the at least two distal elements are closer together) to an open position (wherein the engagement surfaces of the at least two distal elements are further apart), movement between the closed and open position may advance the extension arm of each distal element along its longitudinal axis.

In a second aspect of the present invention, fixation devices are provided that include two pairs of distal elements, wherein the pairs of distal elements are in an opposed orientation so that the engagement surfaces of one pair faces the engagement surfaces of the other pair, and wherein the pairs of distal elements are moveable to engage tissue with the opposed engagement surfaces of the two pairs of distal elements. Thus, the fixation device includes four distal elements, the distal elements functioning in pairs so that each pair of distal elements engages a valve leaflet (in the case of the tissue comprising a valve leaflet) rather than a single distal element engaging each valve leaflet. In some embodiments, the distal elements of at least one of the two pairs are alignable so their longitudinal axes are substantially parallel. Alternatively or in addition, the distal elements of at least one of the two pairs may be rotatable laterally outwardly to a splayed position wherein their longitudinal axes substantially form an angle.

In a third aspect of the present invention, accessories are provided which may be used with fixation devices of the present invention. Such accessories may provide benefits which are similar to increasing the width and/or length of the distal elements. Thus, such accessories may be used with fixation devices of fixed dimension or with fixation devices having distal elements of varying dimensions.

In some embodiments, the accessory comprises a support coupleable with the fixation device, the support having at least two planar sections, each planar section configured to mate with an engagement surface of a distal element when coupled. In some embodiments, wherein the tissue comprises a valve leaflet, the support is configured so that each planar section is positionable against an upstream surface of the valve leaflet while each distal element is positionable against a downstream surface of the valve leaflet. Typically the fixation device is released from a delivery catheter yet temporarily maintained by a tether. Thus, in some embodiments, the support is configured to be advancable along the tether to the fixation device. The tether may be removed from the fixation device while the support is coupled to the fixation device. Thus, the fixation device and support may be left behind to maintain fixation of the tissue.

In a fourth aspect of the present invention, a fixation device is provided having at least two distal elements wherein each of the at least two distal elements has a length along its longitudinal axis, and wherein the length of one of the at least two distal elements is longer than another of the at least two distal elements. In some embodiments, the fixation device has variable length distal elements, wherein each distal element is adjustable to a different length. In other embodiments, the fixation device has fixed length distal elements, wherein each distal element is formed to have a different length. And, in still further embodiments, the fixation device has both fixed and variable length distal elements.

Other aspects of the nature and advantages of the invention are set forth in the detailed description set forth below, taken in conjunction with the drawings.

BRIEF DESCRIPTION OF THE DRAWINGS

FIGS. 8A-8B illustrate an embodiment of distal elements having variable width wherein one or more loops are extendable laterally outwardly.

FIGS. 9A-9B illustrate an embodiment of distal elements having variable width wherein one or more flaps are extendable laterally outwardly.

FIGS. 12A-12B provide a top view of a fixation device having distal elements which are capable of moving to a splayed position.

FIGS. 17A-17B illustrate an embodiment of an accessory for use with fixation devices of the present invention.

FIGS. 18A-18B illustrate an embodiment of distal elements which vary in length and width.

DETAILED DESCRIPTION OF THE INVENTION

1. Fixation Device Overview. The present invention provides methods and devices for grasping, approximating and fixating tissues such as valve leaflets to treat cardiac valve regurgitation, particularly mitral valve regurgitation.

Grasping may be atraumatic which can provide a number of benefits. By atraumatic, it is meant that the devices and methods of the invention may be applied to the valve leaflets and then removed without causing any significant clinical impairment of leaflet structure or function.

The leaflets and valve continue to function substantially the same as before the invention was applied. Thus, some minor penetration or denting of the leaflets may occur using the invention while still meeting the definition of "atraumatic". This enables the devices of the invention to be applied to a diseased valve and, if desired, removed or repositioned without having negatively affected valve function. In addition, it will be understood that in some cases it may be necessary or desirable to pierce or otherwise permanently affect the leaflets during either grasping, fixing or both. In some of these cases, grasping and fixation may be accomplished by a single device. Although a number of embodiments are provided to achieve these results, a general overview of the basic features will be presented herein. Such features are not intended to limit the scope of the invention and are presented with the aim of providing a basis for descriptions of individual embodiments presented later in the application.

Figure 1A:
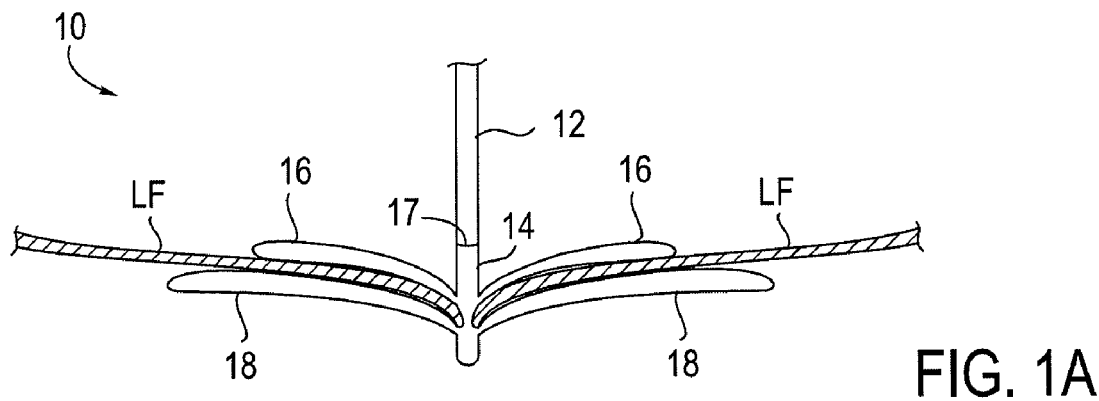
FIG. 1A-1C illustrate grasping of the leaflets with a fixation device, inversion of the distal elements of the fixation device and removal of the fixation device, respectively.

The devices and methods of the invention rely upon the use of an interventional tool that is positioned near a desired treatment site and used to grasp the target tissue. In endovascular applications, the interventional tool is typically an interventional catheter. In surgical applications, the interventional tool is typically an interventional instrument. In some embodiments, fixation of the grasped tissue is accomplished by maintaining grasping with a portion of the interventional tool which is left behind as an implant. While the invention may have a variety of applications for tissue approximation and fixation throughout the body, it is particularly well adapted for the repair of valves, especially cardiac valves such as the mitral valve. Referring to FIG. 1A, an interventional tool 10, having a delivery device, such as a shaft 12, and a fixation device 14, is illustrated having approached the mitral valve MV from the atrial side and grasped the leaflets LF. The mitral valve may be accessed either surgically or by using endovascular techniques, and either by a retrograde approach through the ventricle or by an antegrade approach through the atrium, as described above. For illustration purposes, an antegrade approach is described.

The fixation device 14 is releasably attached to the shaft 12 of the interventional tool 10 at its distal end. When describing the devices of the invention herein, "proximal" shall mean the direction toward the end of the device to be manipulated by the user outside the patient's body, and "distal" shall mean the direction toward the working end of the device that is positioned at the treatment site and away from the user. With respect to the mitral valve, proximal shall refer to the atrial or upstream side of the valve leaflets and distal shall refer to the ventricular or downstream side of the valve leaflets.

The fixation device 14 typically comprises proximal elements 16 (or gripping elements) and distal elements 18 (or fixation elements) which protrude radially outward and are positionable on opposite sides of the leaflets LF as shown so as to capture or retain the leaflets therebetween. The proximal elements 16 may be comprised of cobalt chromium, nitinol or stainless steel, and the distal elements 18 are may be comprised of cobalt chromium or stainless steel, however any suitable materials may be used. The fixation device 14 is coupleable to the shaft 12 by a coupling mechanism 17. The coupling mechanism 17 allows the fixation device 14 to detach and be left behind as an implant to hold the leaflets together in the coapted position.

Figure 1B:
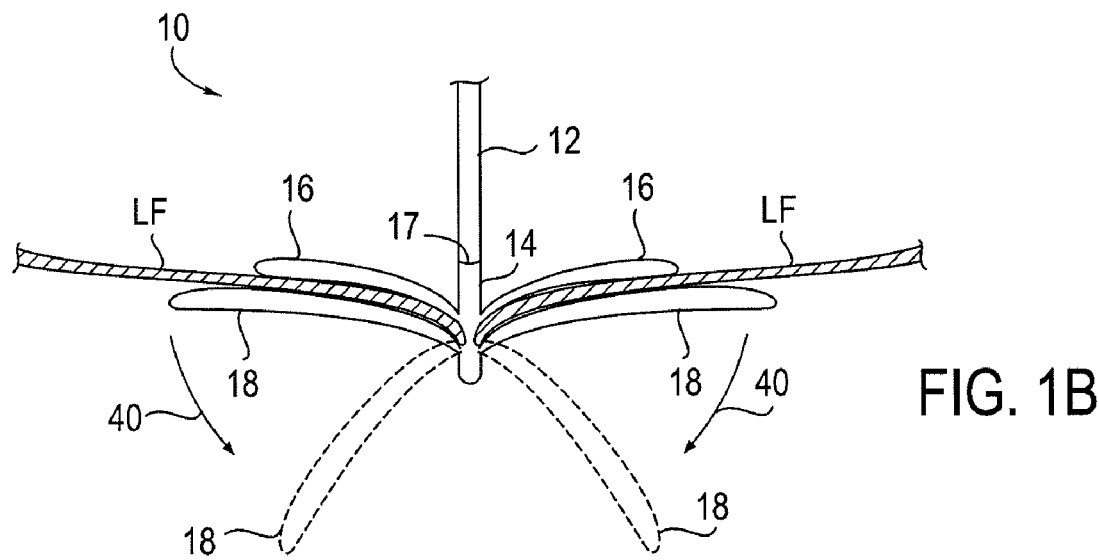
Figure 1C:
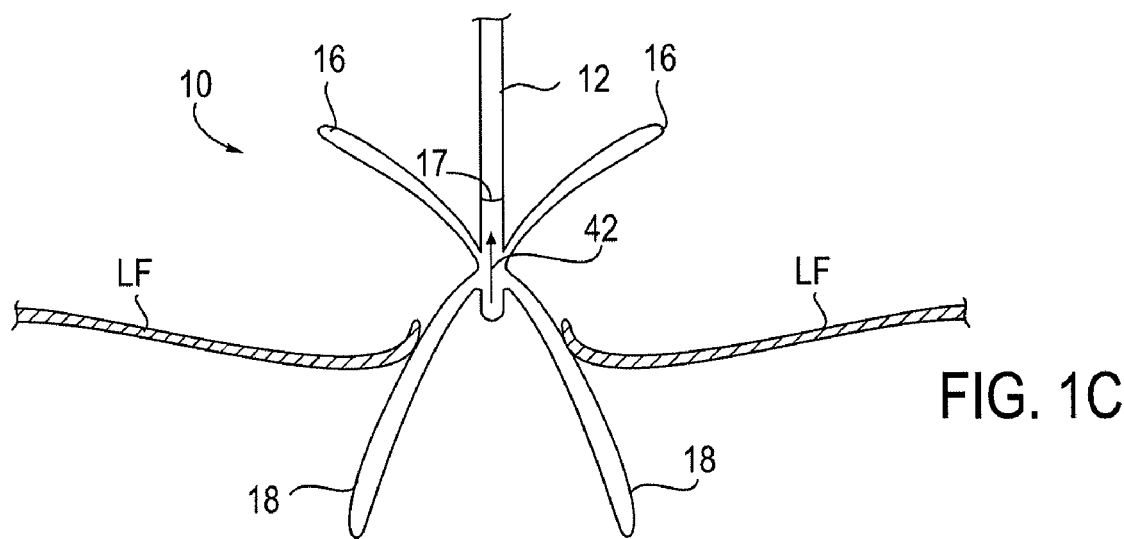

In some situations, it may be desired to reposition or remove the fixation device 14 after the proximal elements 16, distal elements 18, or both have been deployed to capture the leaflets LF. Such repositioning or removal may be desired for a variety of reasons, such as to reapproach the valve in an attempt to achieve better valve function, more optimal positioning of the device 14 on the leaflets, better purchase on the leaflets, to detangle the device 14 from surrounding tissue such as chordae, to exchange the device 14 with one having a different design, or to abort the fixation procedure, to name a few. To facilitate repositioning or removal of the fixation device 14 the distal elements 18 are releasable and optionally invertible to a configuration suitable for withdrawal of the device 14 from the valve without tangling or interfering with or damaging the chordae, leaflets or other tissue. FIG. 1B illustrates inversion wherein the distal elements 18 are moveable in the direction of arrows 40 to an inverted position. Likewise, the proximal elements 16 may be raised, if desired. In the inverted position, the device 14 may be repositioned to a desired orientation wherein the distal elements may then be reverted to a grasping position against the leaflets as in FIG. 1A. Alternatively, the fixation device 14 may be withdrawn (indicated by arrow 42) from the leaflets as shown in FIG. 1C. Such inversion reduces trauma to the leaflets and minimizes any entanglement of the device with surrounding tissues. Once the device 14 has been withdrawn through the valve leaflets, the proximal and distal elements may be moved to a closed position or configuration suitable for removal from the body or for reinsertion through the mitral valve.

Figure 2:
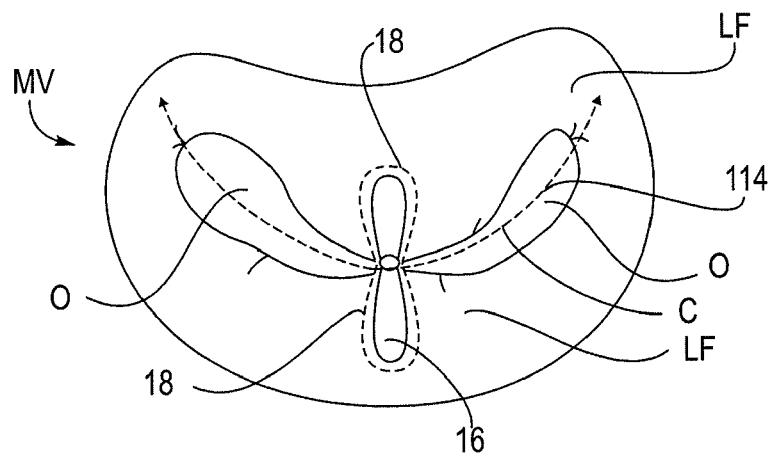
FIG. 2 illustrates the position of the fixation device in a desired orientation relative to the leaflets.

FIG. 2 illustrates the position of the fixation device 14 in a desired orientation in relation to the leaflets LF. This is a short-axis view of the mitral valve MV from the atrial side, therefore, the proximal elements 16 are shown in solid line and the distal elements 18 are shown in dashed line. The proximal and distal elements 16, 18 are positioned to be substantially perpendicular to the line of coaptation C. The device 14 may be moved roughly along the line of coaptation to the location of regurgitation. The leaflets LF are held in place so that during diastole, as shown in FIG. 2, the leaflets LF remain in position between the elements 16, 18 surrounded by openings O which result from the diastolic pressure gradient. Advantageously, leaflets LF are coapted such that their proximal or upstream surfaces are facing each other in a vertical orientation, parallel to the direction of blood flow through mitral valve MV. The upstream surfaces may be brought together so as to be in contact with one another or may be held slightly apart, but will preferably be maintained in the substantially vertical orientation in which the upstream surfaces face each other at the point of coaptation. This simulates the double orifice geometry of a standard surgical bow-tie repair. Color Doppler echo will show if the regurgitation of the valve has been reduced. If the resulting mitral flow pattern is satisfactory, the leaflets may be fixed together in this orientation. If the resulting color Doppler image shows insufficient improvement in mitral regurgitation, the interventional tool 10 may be repositioned. This may be repeated until an optimal result is produced wherein the leaflets LF are held in place. Once the leaflets are coapted in the desired arrangement, the fixation device 14 is then detached from the shaft 12 and left behind as an implant to hold the leaflets together in the coapted position.

Figure 3:
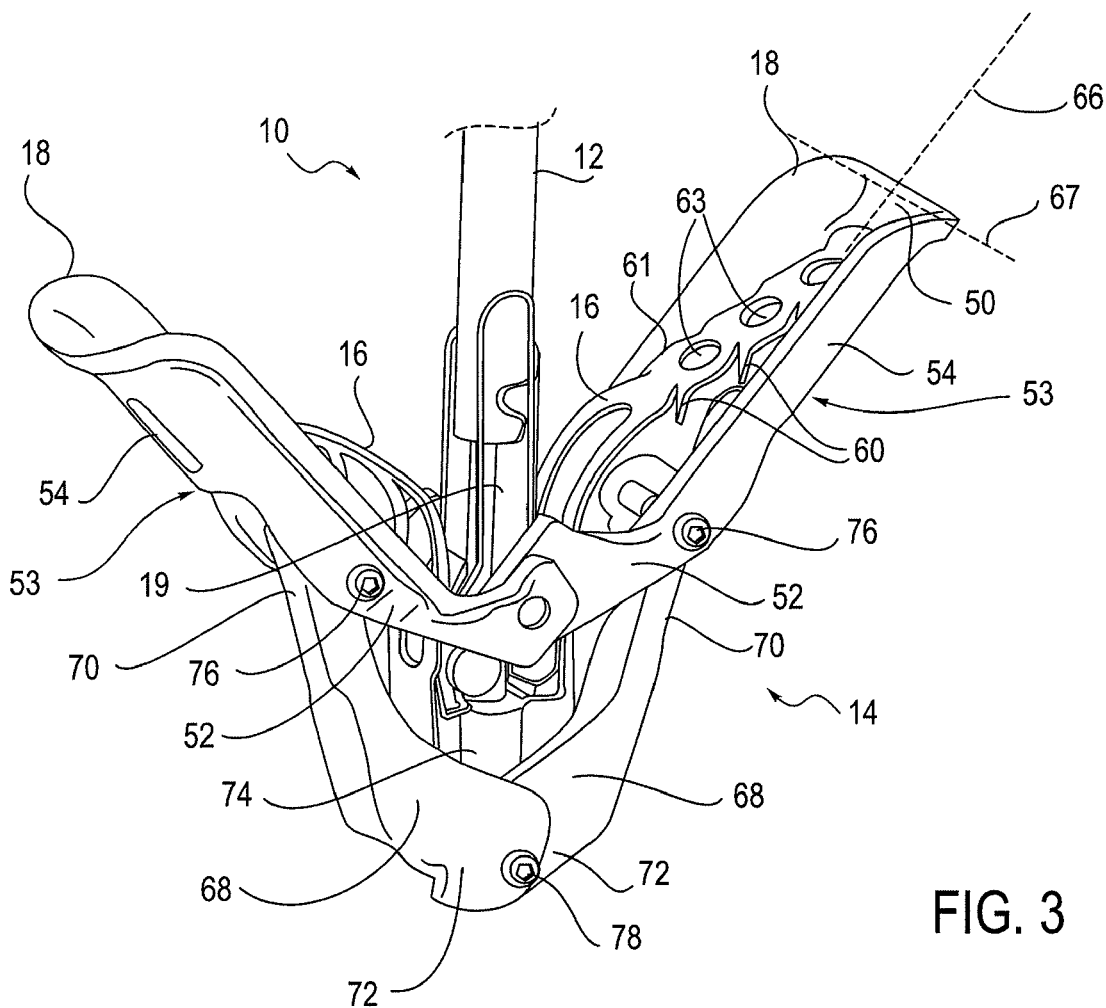
FIG. 3 illustrates another embodiment of the fixation device of the present invention.

FIG. 3 illustrates an embodiment of a fixation device 14. Here, the fixation device 14 is shown coupled to a shaft 12 to form an interventional tool 10. The fixation device 14 includes a coupling member 19 and a pair of opposed distal elements 18. The distal elements 18 comprise elongate arms 53, each arm having a proximal end 52 rotatably connected to the coupling member 19 and a free end 54. The free ends 54 have a rounded shape to minimize interference with and trauma to surrounding tissue structures. Each free end 54 may define a curvature about two axes, one being a longitudinal axis 66 of arms 53. Thus, engagement surfaces 50 have a cupped or concave shape to surface area in contact with tissue and to assist in grasping and holding the valve leaflets. This further allows arms 53 to nest around the shaft 12 in a closed position to minimize the profile of the device. Arms 53 may be at least partially cupped or curved inwardly about their longitudinal axes 66. Also, each free end 54 may define a curvature about an axis 67 perpendicular to longitudinal axis 66 of arms 53. This curvature is a reverse curvature along the most distal portion of the free end 54. Likewise, the longitudinal edges of the free ends 54 may flare outwardly. Both the reverse curvature and flaring minimize trauma to the tissue engaged therewith. Arms 53 further include a plurality of openings to enhance grip and to promote tissue ingrowth following implantation.

The valve leaflets are grasped between the distal elements 18 and proximal elements 16. In some embodiments, the proximal elements 16 are flexible, resilient, and cantilevered from coupling member 19. The proximal elements are preferably resiliently biased toward the distal elements. Each proximal element 16 is shaped and positioned to be at least partially recessed within the concavity of the distal element 18 when no tissue is present. When the fixation device 14 is in the open position, the proximal elements 16 are shaped such that each proximal element 16 is separated from the engagement surface 50 near the proximal end 52 of arm 53 and slopes toward the engagement surface 50 near the free end 54 with the free end of the proximal element contacting engagement surface 50, as illustrated in FIG. 3. This shape of the proximal elements 16 accommodates valve leaflets or other tissues of varying thicknesses.

Proximal elements 16 include a plurality of openings 63 and scalloped side edges 61 to increase grip on tissue. The proximal elements 16 optionally include frictional accessories, frictional features or grip-enhancing elements to assist in grasping and/or holding the leaflets. In some embodiments, the frictional accessories comprise barbs 60 having tapering pointed tips extending toward engagement surfaces 50. It may be appreciated that any suitable frictional accessories may be used, such as prongs, windings, bands, barbs, grooves, channels, bumps, surface roughening, sintering, high-friction pads, coverings, coatings or a combination of these. Optionally, magnets may be present in the proximal and/or distal elements. It may be appreciated that the mating surfaces will be made from or will include material of opposite magnetic charge to cause attraction by magnetic force. For example, the proximal elements and distal elements may each include magnetic material of opposite charge so that tissue is held under constant compression between the proximal and distal elements to facilitate faster healing and ingrowth of tissue. Also, the magnetic force may be used to draw the proximal elements 16 toward the distal elements 18, in addition to or alternatively to biasing of the proximal elements toward the distal elements. This may assist in deployment of the proximal elements 16. In another example, the distal elements 18 each include magnetic material of opposite charge so that tissue positioned between the distal elements 18 is held therebetween by magnetic force.

The fixation device 14 also includes an actuation mechanism 58. In this embodiment, the actuation mechanism 58 comprises two link members or legs 68, each leg 68 having a first end 70 which is rotatably joined with one of the distal elements 18 at a riveted joint 76 and a second end 72 which is rotatably joined with a stud 74. The legs 68 may be comprised of a rigid or semi-rigid metal or polymer such as Elgiloy®, cobalt chromium or stainless steel, however any suitable material may be used. While in the embodiment illustrated both legs 68 are pinned to stud 74 by a single rivet 78, it may be appreciated, however, that each leg 68 may be individually attached to the stud 74 by a separate rivet or pin. The stud 74 is joinable with an actuator rod 64 (not shown) which extends through the shaft 12 and is axially extendable and retractable to move the stud 74 and therefore the legs 68 which rotate the distal elements 18 between closed, open and inverted positions. Likewise, immobilization of the stud 74 holds the legs 68 in place and therefore holds the distal elements 18 in a desired position. The stud 74 may also be locked in place by a locking feature.

In any of the embodiments of fixation device 14 disclosed herein, it may be desirable to provide some mobility or flexibility in distal elements 18 and/or proximal elements 16 in the closed position to enable these elements to move or flex with the opening or closing of the valve leaflets. This provides shock absorption and thereby reduces force on the leaflets and minimizes the possibility for tearing or other trauma to the leaflets. Such mobility or flexibility may be provided by using a flexible, resilient metal or polymer of appropriate thickness to construct the distal elements 18. Also, the locking mechanism of the fixation device (described below) may be constructed of flexible materials to allow some slight movement of the proximal and distal elements even when locked. Further, the distal elements 18 can be connected to the coupling mechanism 19 or to actuation mechanism 58 by a mechanism that biases the distal element into the closed position (inwardly) but permits the arms to open slightly in response to forces exerted by the leaflets. For example, rather than being pinned at a single point, these components may be pinned through a slot that allowed a small amount of translation of the pin in response to forces against the arms. A spring is used to bias the pinned component toward one end of the slot.

Figure 4A:
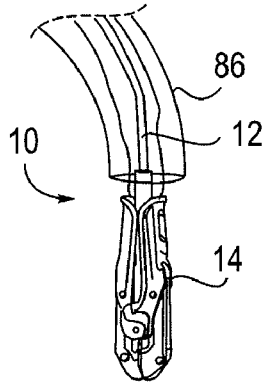
FIGS. 4A-4B, 5A-5B, 6A-6B, 7A-7B illustrate embodiments of a fixation device in various possible positions during introduction and placement of the device within the body to perform a therapeutic procedure.
Figure 4B:
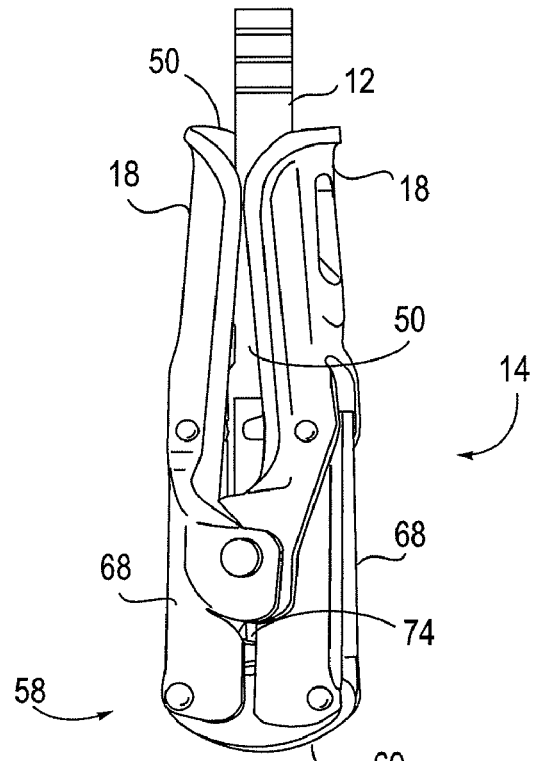

FIGS. 4A-4B, 5A-5B, 6A-6B, 7A-7B illustrate embodiments of the fixation device 14 of FIG. 3 in various possible positions during introduction and placement of the device 14 within the body to perform a therapeutic procedure. FIG. 4A illustrates an embodiment of an interventional tool 10 delivered through a catheter 86. It may be appreciated that the interventional tool 10 may take the form of a catheter, and likewise, the catheter 86 may take the form of a guide catheter or sheath. However, in this example the terms interventional tool 10 and catheter 86 will be used. The interventional tool 10 comprises a fixation device 14 coupled to a shaft 12 and the fixation device 14 is shown in the closed position. FIG. 4B illustrates a similar embodiment of the fixation device of FIG. 4A in a larger view. In the closed position, the opposed pair of distal elements 18 are positioned so that the engagement surfaces 50 face each other. Each distal element 18 comprises an elongate arm 53 having a cupped or concave shape so that together the arms 53 surround the shaft 12 and optionally contact each other on opposite sides of the shaft. This provides a low profile for the fixation device 14 which is readily passable through the catheter 86 and through any anatomical structures, such as the mitral valve. In addition, FIG. 4B further includes an actuation mechanism 58. In this embodiment, the actuation mechanism 58 comprises two legs 68 which are each movably coupled to a base 69. The base 69 is joined with an actuator rod 64 which extends through the shaft 12 and is used to manipulate the fixation device 14. In some embodiments, the actuator rod 64 attaches directly to the actuation mechanism 58, particularly the base 69. However, the actuator rod 64 may alternatively attach to a stud 74 which in turn is attached to the base 69. In some embodiments, the stud 74 is threaded so that the actuator rod 64 attaches to the stud 74 by a screw-type action. However, the rod 64 and stud 74 may be joined by any mechanism which is releasable to allow the fixation device 14 to be detached from shaft 12.

Figure 5A:
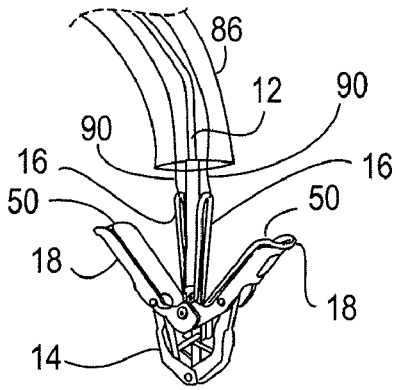
Figure 5B:
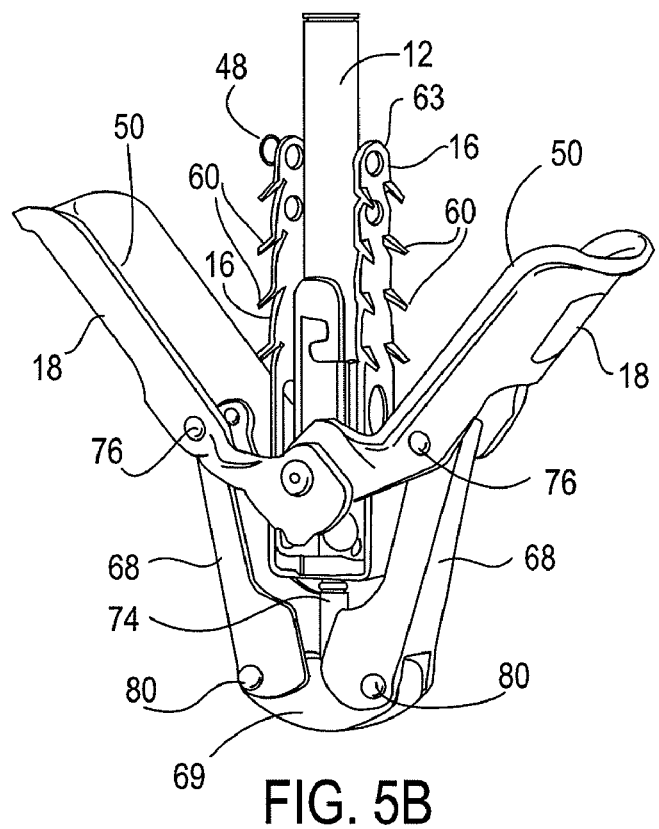

FIGS. 5A-5B illustrate the fixation device 14 in the open position. In the open position, the distal elements 18 are rotated so that the engagement surfaces 50 face a first direction. Distal advancement of the stud 74 relative to coupling member 19 by action of the actuator rod 64 applies force to the distal elements 18 which begin to rotate around joints 76 due to freedom of movement in this direction. Such rotation and movement of the distal elements 18 radially outward causes rotation of the legs 68 about joints 80 so that the legs 68 are directly slightly outwards. The stud 74 may be advanced to any desired distance correlating to a desired separation of the distal elements 18. In the open position, engagement surfaces 50 are disposed at an acute angle relative to shaft 12, and are preferably at an angle of between 90 and 180 degrees relative to each other. In one embodiment, in the open position the free ends 54 of arms 53 have a span therebetween of about 10-20 mm, usually about 12-18 mm, and preferably about 14-16 mm.

Proximal elements 16 are typically biased outwardly toward arms 53. The proximal elements 16 may be moved inwardly toward the shaft 12 and held against the shaft 12 with the aid of proximal element lines 90 which can be in the form of sutures, wires, nitinol wire, rods, cables, polymeric lines, or other suitable structures. The proximal element lines 90 may be connected with the proximal elements 16 by threading the lines 90 in a variety of ways. When the proximal elements 16 have a loop shape, as shown in FIG. 5A, the line 90 may pass through the loop and double back. When the proximal elements 16 have an elongate solid shape, as shown in FIG. 5B, the line 90 may pass through one or more of the openings 63 in the element 16. Further, a line loop 48 may be present on a proximal element 16, also illustrated in FIG. 5B, through which a proximal element line 90 may pass and double back. Such a line loop 48 may be useful to reduce friction on proximal element line 90 or when the proximal elements 16 are solid or devoid of other loops or openings through which the proximal element lines 90 may attach. A proximal element line 90 may attach to the proximal elements 16 by detachable means which would allow a single line 90 to be attached to a proximal element 16 without doubling back and would allow the single line 90 to be detached directly from the proximal element 16 when desired. Examples of such detachable means include hooks, snares, clips or breakable couplings, to name a few. By applying sufficient tension to the proximal element line 90, the detachable means may be detached from the proximal element 16 such as by breakage of the coupling. Other mechanisms for detachment may also be used. Similarly, a lock line 92 may be attached and detached from a locking mechanism by similar detachable means.

In the open position, the fixation device 14 can engage the tissue which is to be approximated or treated. This embodiment is adapted for repair of the mitral valve using an antegrade approach from the left atrium. The interventional tool 10 is advanced through the mitral valve from the left atrium to the left ventricle. The distal elements 18 are oriented to be perpendicular to the line of coaptation and then positioned so that the engagement surfaces 50 contact the ventricular surface of the valve leaflets, thereby grasping the leaflets. The proximal elements 16 remain on the atrial side of the valve leaflets so that the leaflets lie between the proximal and distal elements. In this embodiment, the proximal elements 16 have frictional accessories, such as barbs 60 which are directed toward the distal elements 18. However, neither the proximal elements 16 nor the barbs 60 contact the leaflets at this time.

The interventional tool 10 may be repeatedly manipulated to reposition the fixation device 14 so that the leaflets are properly contacted or grasped at a desired location. Repositioning is achieved with the fixation device in the open position. In some instances, regurgitation may also be checked while the device 14 is in the open position. If regurgitation is not satisfactorily reduced, the device may be repositioned and regurgitation checked again until the desired results are achieved.

Figure 6A:
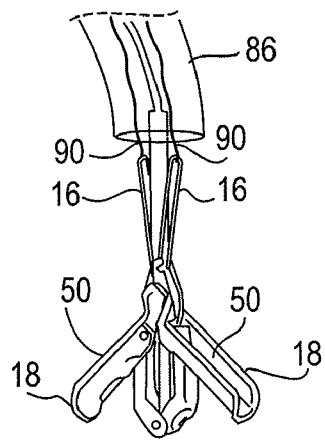
Figure 6B:
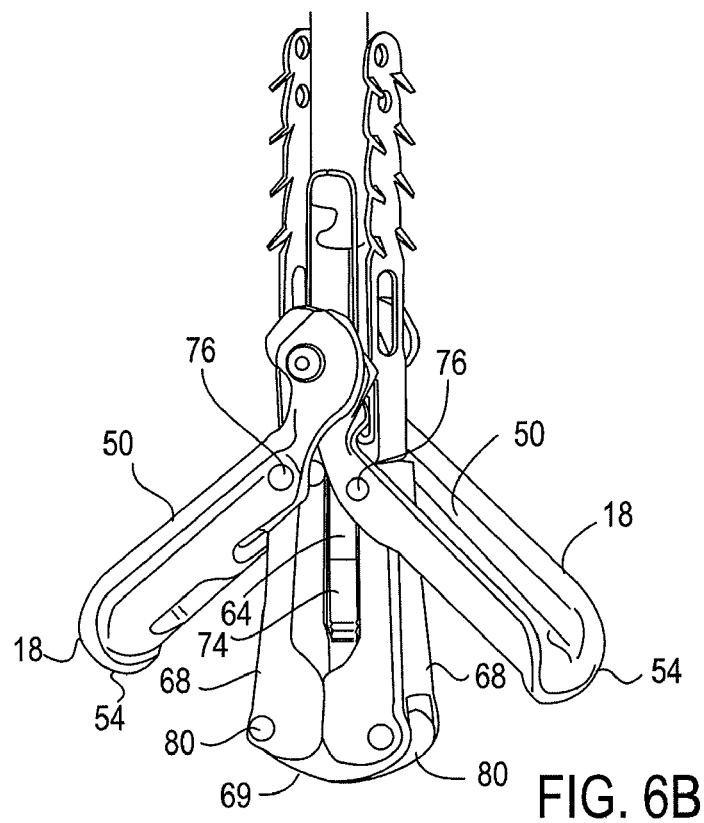

It may also be desired to invert the fixation device 14 to aid in repositioning or removal of the fixation device 14. FIGS. 6A-6B illustrate the fixation device 14 in the inverted position.

By further advancement of stud 74 relative to coupling member 19, the distal elements 18 are further rotated so that the engagement surfaces 50 face outwardly and free ends 54 point distally, with each arm 53 forming an obtuse angle relative to shaft 12. The angle between arms 53 is preferably in the range of about 270 to 360 degrees. Further advancement of the stud 74 further rotates the distal elements 18 around joints 76. This rotation and movement of the distal elements 18 radially outward causes rotation of the legs 68 about joints 80 so that the legs 68 are returned toward their initial position, generally parallel to each other. The stud 74 may be advanced to any desired distance correlating to a desired inversion of the distal elements 18. Preferably, in the fully inverted position, the span between free ends 54 is no more than about 20 mm, usually less than about 16 mm, and preferably about 12-14 mm. In this illustration, the proximal elements 16 remain positioned against the shaft 12 by exerting tension on the proximal element lines 90. Thus, a relatively large space may be created between the elements 16, 18 for repositioning. In addition, the inverted position allows withdrawal of the fixation device 14 through the valve while minimizing trauma to the leaflets. Engagement surfaces 50 provide an atraumatic surface for deflecting tissue as the fixation device is refracted proximally. It should be further noted that barbs 60 are angled slightly in the distal direction (away from the free ends of the proximal elements 16), reducing the risk that the barbs will catch on or lacerate tissue as the fixation device is withdrawn.

Figure 7A:
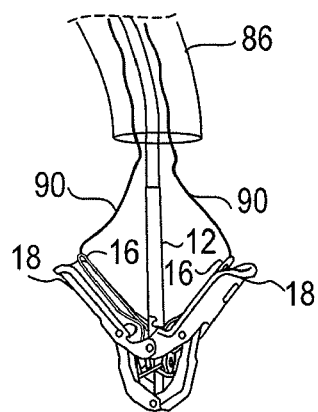
Figure 7B:
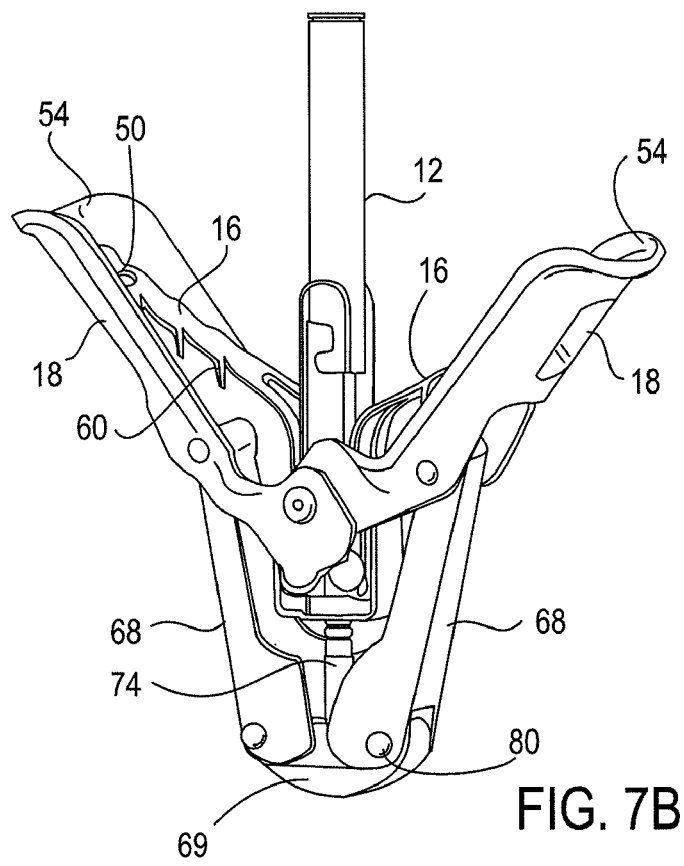

Once the fixation device 14 has been positioned in a desired location against the valve leaflets, the leaflets may then be captured between the proximal elements 16 and the distal elements 18. FIGS. 7A-7B illustrate the fixation device 14 in such a position. Here, the proximal elements 16 are lowered toward the engagement surfaces 50 so that the leaflets are held therebetween. In FIG. 7B, the proximal elements 16 are shown to include barbs 60 which may be used to provide atraumatic gripping of the leaflets. Alternatively, larger, more sharply pointed barbs or other penetration structures may be used to pierce the leaflets to more actively assist in holding them in place. This position is similar to the open position of FIGS. 5A-5B, however the proximal elements 16 are now lowered toward arms 53 by releasing tension on proximal element lines 90 to compress the leaflet tissue therebetween. At any time, the proximal elements 16 may be raised and the distal elements 18 adjusted or inverted to reposition the fixation device 14, if regurgitation is not sufficiently reduced.

After the leaflets have been captured between the proximal and distal elements 16, 18 in a desired arrangement, the distal elements 18 may be locked to hold the leaflets in this position or the fixation device 14 may be returned to or toward a closed position.

It may be appreciated that the fixation devices 14 of the present invention may have any or all of the above described functions and features. For example, the fixation devices 14 may or may not be moveable to an inverted position. Or, the fixation devices 14 may or may not include proximal elements 16. Thus, the above described aspects of the fixation devices 14 are simply various embodiments and are not intended to limit the scope of the present invention.

2. Variable Width Distal Elements. The width of one or more distal elements 18 of a fixation device 14 may be varied to increase the surface area and therefore increase the area of contact with tissue to be fixated, such as a valve leaflet. In some embodiments, the width is increased once the leaflets have been grasped. In other embodiments, the width is increased prior to grasping of the leaflets. Although it is typically desired to increase the width of the distal elements 18 to increase purchase size and distribute fixation forces, in some instances the variable width distal elements 18 may be used to decrease the width, either prior to leaflet grasping or while the leaflets are grasped.

FIGS. 8A-8B illustrate an embodiment of distal elements 18 having a variable width. In this embodiment, each distal element 18 has one or more loops 100 which are extendable laterally outward in a direction perpendicular to longitudinal axis 66. FIG. 8A illustrates the loops 100 in a retracted position, wherein the distal elements 18 each have a width determined by the size of the distal element 18 itself. In this embodiment, the loops 100 are disposed on a surface of the distal elements 18 opposite the engagement surfaces 50 when in the retracted position. However, it may be appreciated that the loops 100 may be disposed on the engagement surfaces 50 or within the distal elements 18 themselves. FIG. 8B illustrates the loops 100 in an expanded position wherein the loops 100 extend laterally outward in a direction perpendicular to longitudinal axis 66. Expansion may be active or passive. The loops 100 may be comprised of any suitable material including wire, polymer, shape-memory alloy, Nitinol™, suture, or fiber, to name a few. Further, it may be appreciated that any number of loops 100 may be present, the loops 100 may extend any distance and the loops 100 may expand on one side of a distal element and not the other.

FIGS. 9A-9B illustrate another embodiment of a fixation device 14 having distal elements 18 of variable width; here, the fixation device 14 is shown grasping a leaflet LF. In this embodiment, each distal element 18 has one or more flaps 104 which are extendable laterally outward in a direction perpendicular to longitudinal axis 66. FIG. 9A illustrates the flaps 104 in a retracted position wherein the flaps 104 are substantially disposed within the distal elements 18 themselves. It may be appreciated however that the flaps 104 may be folded or curved so that the flaps are substantially disposed on the engagement surfaces 50 or on a surface of the distal elements 18 opposite the engagement surfaces 50. FIG. 9B illustrates the flaps 104 in an expanded position wherein the flaps 104 extend laterally outward in a direction perpendicular to longitudinal axis 66. Expansion may be active or passive. The flaps 104 may be comprised of any suitable material including polymer, mesh, metal, shape-memory alloy or a combination of these, to name a few. Further, it may be appreciated that any number of flaps 104 may be present, the flaps 104 may extend any distance and the flaps 104 may expand on one side of a distal element and not the other.

Figure 10A:
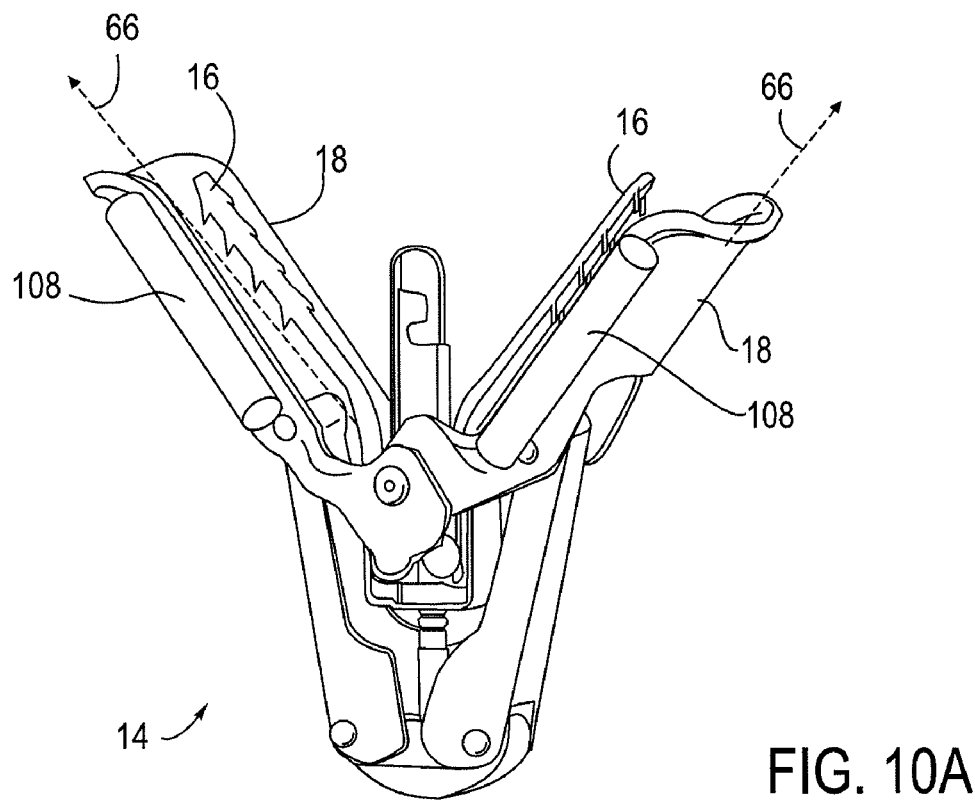
FIGS. 10A-10B illustrate an embodiment of distal elements having variable width wherein one or more pontoons are expandable laterally outwardly.
Figure 10B:
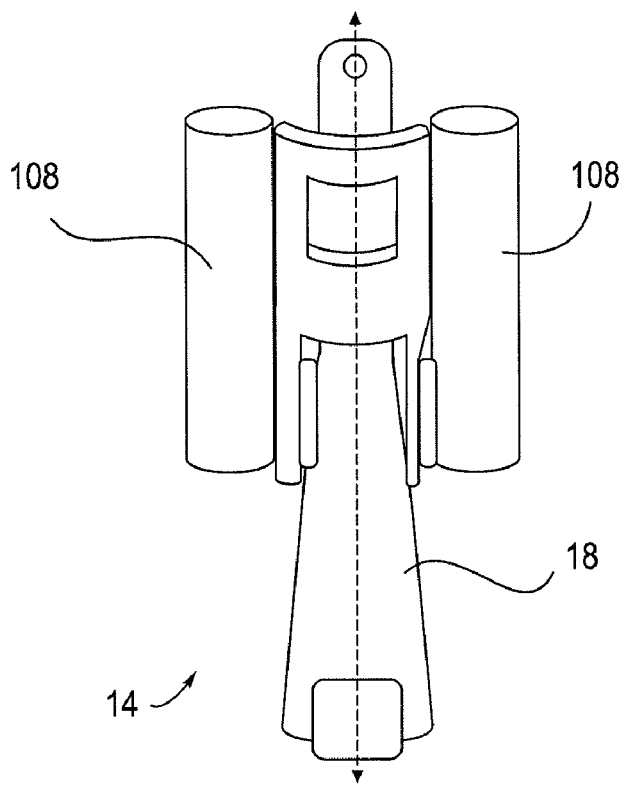

FIGS. 10A-10B illustrate yet another embodiment of a fixation device 14 having distal elements 18 of variable width. In this embodiment, each distal element 18 has one or pontoons 108 which are expandable laterally outward in a direction perpendicular to longitudinal axis 66. FIG. 10A provides a perspective view of a fixation device 14 having expandable pontoons 108 wherein the pontoons 108 are in an expanded state. FIG. 10B provides a side view of the fixation device 14 of FIG. 10B. Here, the increase in width of the distal element 18 due to the pontoon 108 may be readily seen. The pontoons 108 may be expanded by any means, such as by inflation with liquid or gas, such as by inflation with saline solution. Such expansion may be active or passive. The pontoons 108 may be comprised of any suitable material such as a flexible polymer or plastic. Further, it may be appreciated that any number of pontoons 108 may be present, the pontoons 108 may extend any distance and a pontoon 108 may expand on one side of a distal element and not the other.

3. Splayed Distal Elements. In some embodiments, the fixation device 14 includes additional distal elements 18 that assist in grasping of tissue, such as a valve leaflet. For example, the fixation device 14 may include four distal elements 18 wherein a pair of distal elements 18 grasp each side of the leaflet. The pairs of distal elements 18 may have any arrangement, however in some embodiments the distal elements 18 of each pair rotated laterally outwardly to a splayed position. This increases the area of contact with the tissue to be fixated and distributes the fixation forces across a broader portion of the tissue. Typically, the pairs of distal elements are splayed prior to grasping of the leaflets, however such splaying may be achieved after grasping.

Figure 11A:
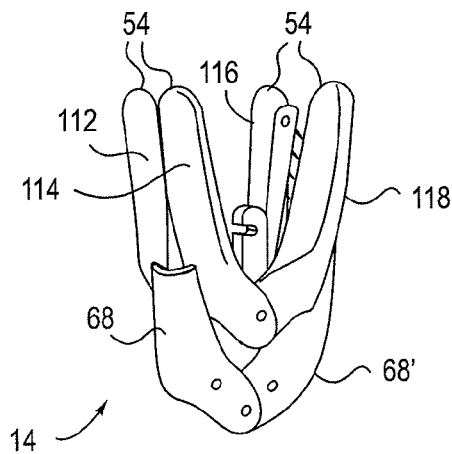
FIGS. 11A-11B provide a perspective view of a fixation device having distal elements which are capable of moving to a splayed position.
Figure 11B:
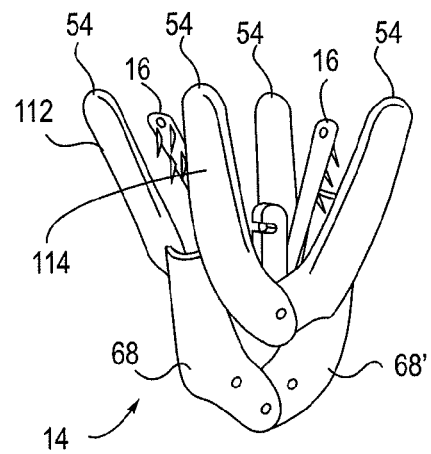

FIGS. 11A-11B provide a perspective view of an embodiment of a fixation device 14 having a first distal element 112, a second distal element 114, a third distal element 116 and a fourth distal element 118. The distal elements 112, 114, 116, 118 are arranged in pairs so that the first and second distal elements 112, 114 are connected with one leg 68 and the third and fourth distal elements 116, 118 are connected with the other leg 68' allowing the distal elements to grasp in pairs. FIG. 11A illustrates the fixation device 14 in a closed position wherein the distal elements 112, 114, 116, 118 are in substantially parallel alignment. FIG. 11B illustrates the fixation device 14 in an open position wherein the distal elements 112, 114, 116, 118 are splayed apart. Here, the first and second distal elements 114 are rotated laterally outwardly so that the free ends 54 are moved away from each other. Such splaying may be achieved as a result of opening the fixation device 14 or may be achieved separately from the opening and closing mechanism. In this embodiment, the fixation device 14 includes two proximal elements 16, each proximal element 16 facing a pair of distal elements. It may be appreciated that any number of proximal elements 16, if any, may be present, including a corresponding proximal element for each distal element. Finally, the distal elements 112, 114, 116, 118 may be splayed to separate the distal elements by any distance and the distance may be fixed or variable. Further, the distal elements 112, 114, 116, 118 may be returned to the substantially parallel alignment.

Figure 11C:
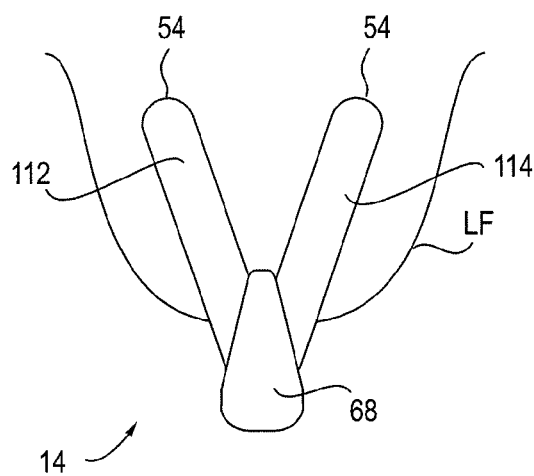
FIGS. 11C-11D provide a side view of the fixation device of FIGS. 11A-11B plicating tissue of a leaflet.
Figure 11D:
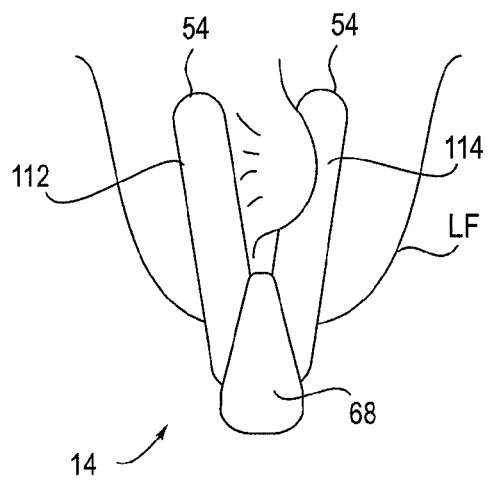

FIG. 11C provides a side view of the fixation device 14 of FIGS. 11A-11B capturing valve leaflets LF in a coapted position. The fixation device 14 is shown in the splayed position wherein the distal elements 112, 114 are rotated laterally outwardly so that the free ends 54 are moved away from each other. It may be appreciated the proximal element 16 is disposed on the opposite side of the leaflet LF and therefore shielded from view. Return of the distal elements 112, 114 toward the substantially parallel alignment, as illustrated in FIG. 11D, may capture tissue between the distal elements 112, 114, plicating the leaflet LF as shown. Such plication may be desired for optimal treatment of the diseased valve.

FIGS. 12A-12B provide a top view of another embodiment of a fixation device 14 having a first distal element 112, a second distal element 114, a third distal element 116 and a fourth distal element 118. FIG. 12A illustrates the fixation device 14 in a closed position wherein the distal elements 112, 114, 116, 118 are in substantially parallel alignment. FIG. 12B illustrates the fixation device 14 in an open position wherein the distal elements 112, 114, 116, 118 are splayed apart. Here, the first and second distal elements 114 are rotated laterally outwardly so that the free ends 54 are moved away from each other. Again, such splaying may be achieved as a result of opening the fixation device 14 or may be achieved separately from the opening and closing mechanism. And, the distal elements 112, 114, 116, 118 may be splayed to separate the distal elements by any distance and the distance may be fixed or variable. Further, the distal elements 112, 114, 116, 118 may be returned to the substantially parallel alignment. Again, it may be appreciated that return of the distal elements toward the substantially parallel alignment may capture tissue between the distal elements, plicating the leaflet.

4. Variable Length Distal Elements. The length of one or more distal elements 18 of a fixation device 14 may be varied to increase the surface area and therefore increase the area of contact with tissue to be fixated, such as a valve leaflet. In some embodiments, the length is increased once the leaflets have been grasped. In other embodiments, the length is increased prior to grasping of the leaflets. Although it is typically desired to increase the length of the distal elements 18 to increase purchase size and distribute fixation forces, in some instances the variable length distal elements 18 may be used to decrease the length, either prior to leaflet grasping or while the leaflets are grasped.

Figure 13A:
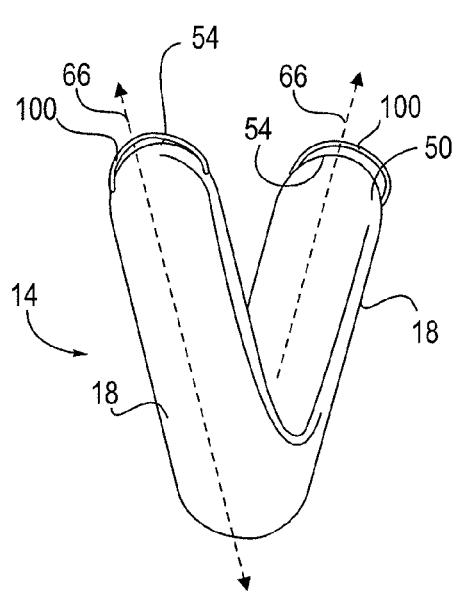
FIGS. 13A-13B illustrate an embodiment of distal elements having variable length wherein one or more loops are extendable outwardly.
Figure 13B:
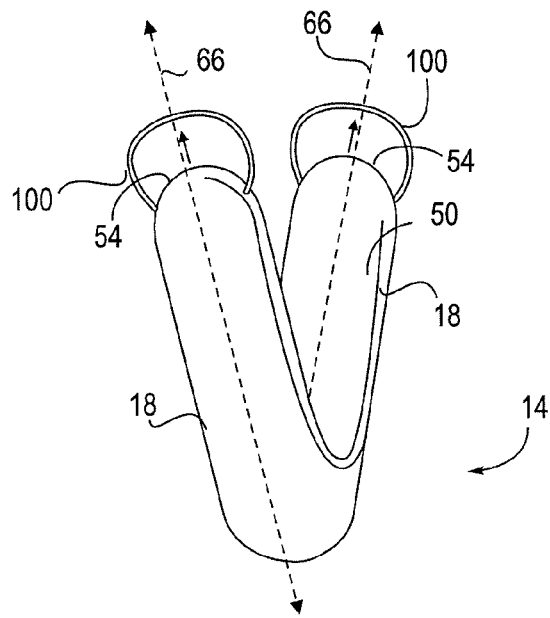

FIGS. 13A-13B illustrate an embodiment of distal elements 18 having a variable length. In this embodiment, each distal element 18 has one or more loops 100 which are extendable outwardly from the free ends 54 along longitudinal axis 66. FIG. 13A illustrates the loops 100 in a refracted position, wherein the distal elements 18 each have a length determined substantially by the length of the distal element 18 itself. In this embodiment, the loops 100 are retracted within the distal elements 18 themselves. However, it may be appreciated that the loops 100 may be disposed on the engagement surfaces 50 or on a surface opposite the engagement surfaces 50. FIG. 13B illustrates the loops 100 in an expanded position wherein the loops 100 extend outwardly along longitudinal axis 66. Expansion may be active or passive. The loops 100 may be comprised of any suitable material including wire, polymer, shape-memory alloy, Nitinol™, suture, or fiber, to name a few. Further, it may be appreciated that any number of loops 100 may be present and the loops 100 may extend any distance.

Figure 14A:
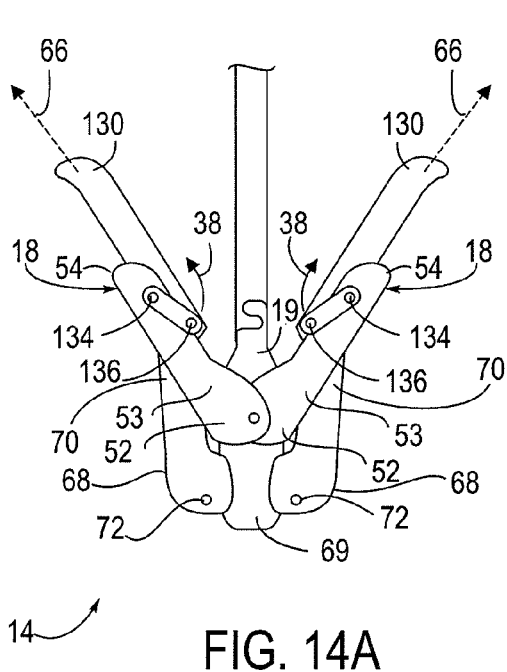
FIGS. 14A-14B, 15 illustrate embodiments of distal elements having variable length wherein the distal elements include extension arms.
Figure 14B:
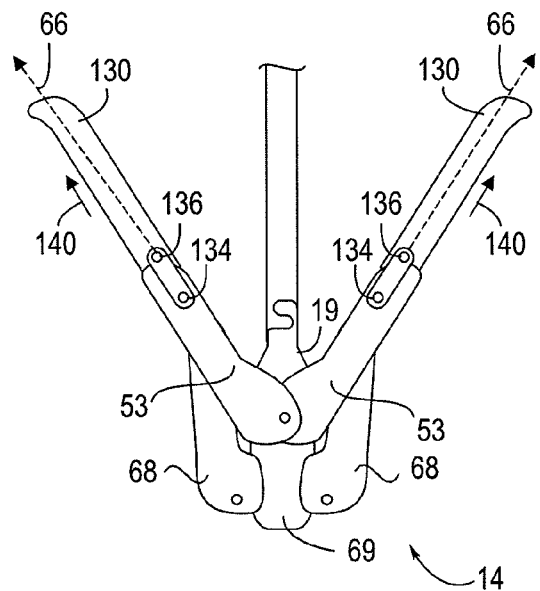

FIGS. 14A-14B illustrate another embodiment of a fixation device 14 having distal elements 18 of variable length. In this embodiment, the fixation device 14 includes a coupling member 19 and a pair of opposed distal elements 18, wherein each distal element 18 is comprised of an elongate arm 53 which is coupled with an extension arm 130. Each elongate arm 53 has a proximal end 52 rotatably connected to the coupling member 19 and a free end 54. The extension arm 130 is coupled with the elongate arm 53 near the free end 54 to lengthen the distal element in the direction of a longitudinal axis 66. Each elongate arm 53 is also coupled with a leg 68, each leg 68 having a first end 70 which is rotatably joined with one of the distal elements 18 and a second end 72 which is rotatably joined with a base 69.

In this embodiment, the extension arm 130 is coupled with the elongate arm 53 by a cam 132. The leg 68 is joined with the arm 53 and cam 132 at a first joint 134 and the extension arm 130 is joined with the cam 132 at a second joint 136. Rotation of the cam 132 in the direction of arrows 138, advances the extension arm 130 along the longitudinal axis 66. FIG. 14B shows the cams 132 rotated so that the extension arms 130 are extended in the direction of arrows 140. The cams 132 may rotate due to motion of the fixation device 14 between an open and closed position, or rotation of the cams 132 may occur due to actuation of a mechanism. The extension arms 130 may be comprised of any suitable material, particularly a material similar to that of the elongate arms 53. Further, it may be appreciated the extension arms 130 may have any length and may extend any distance.

Figure 15:
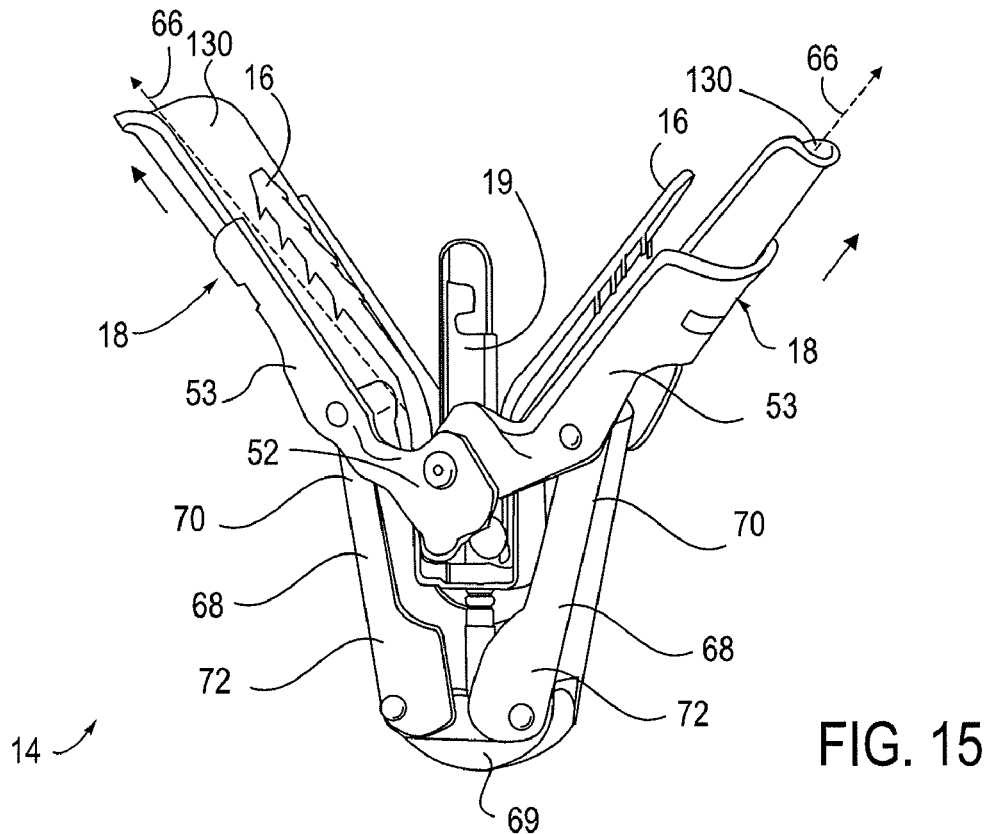

FIG. 15 illustrates another embodiment of a fixation device 14 having distal elements 18 of variable length. In this embodiment, each distal element 18 comprises an elongate arm 53 coupled with an extension arm 130. Each elongate arm 53 has a proximal end 52 rotatably connected to the coupling member 19 and a free end 54. The extension arm 130 is coupled with the elongate arm 53 near the free end 54 to lengthen the distal element in the direction of a longitudinal axis 66. Each elongate arm 53 is also coupled with a leg 68, each leg 68 having a first end 70 which is rotatably joined with one of the distal elements 18 and a second end 72 which is rotatably joined with a base 69. In this embodiment, each extension arm 130 is disposed within a corresponding elongate arm 53 and may be extended beyond the free end 54 by advancement out of the elongate arm 53. Likewise, the extension arm 130 may be retracted back into the elongate arm 53.

In some embodiments, the extension arms 130 are extended by action of the fixation device 14 moving toward an open position and are retracted by action of the fixation device 14 moving toward a closed position. Extension and retraction may be active or passive and the extension arms 130 may be extended any distance.

Figure 16:
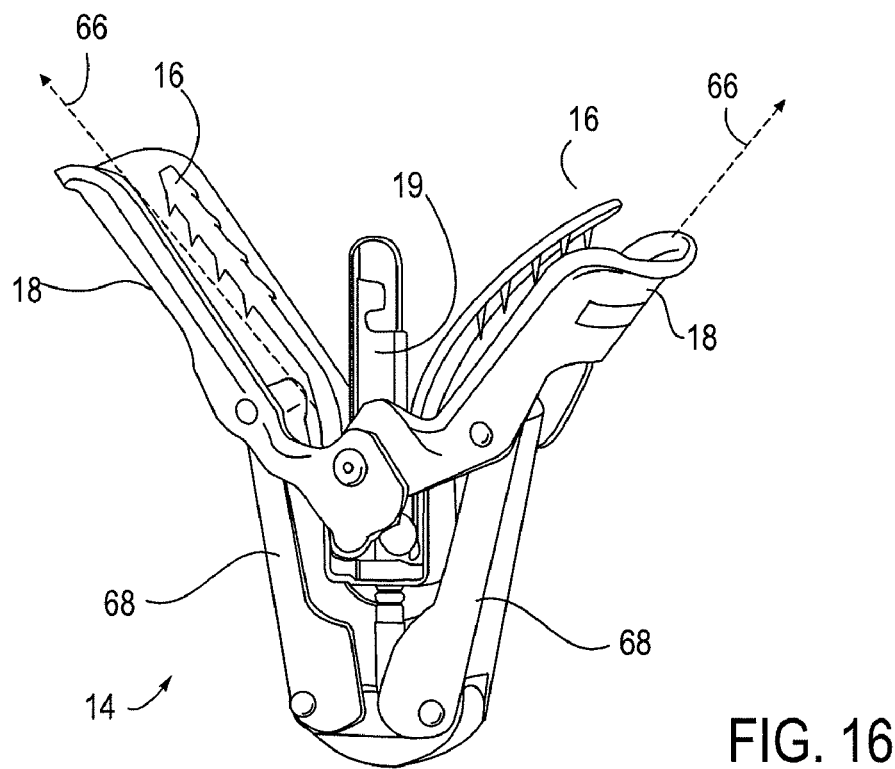
FIG. 16 illustrates an embodiment of the fixation device having distal elements of different lengths.

5. Differing Length Distal Elements. In some instances, it may be desired to grasp or fix tissue or valve leaflets together with a fixation device 14 wherein the distal elements 18 are of differing length. This may be achieved with a fixation device 14 having variable length distal elements 18, wherein each distal element 18 is adjusted to a different length. Or, this may be achieved with a fixation device 14 having distal elements 18 of fixed length, wherein each distal element 18 is formed to have a different length. An example of such a fixation device is illustrated in FIG. 16. As shown, the fixation device 14 includes two distal elements 18, each joined with a coupling member 18 and a leg 68 wherein actuation of the legs 68 move the distal elements 18 between at least an open and closed position. In this example, one of the distal elements 18 is shown to be longer than the other. The fixation device 14 may also include proximal elements 14. Proximal elements 16 may be of the same dimensions or one may be longer than the other to correspond with the distal elements 18 to which they mate.

6. Accessories. One or more accessories may be used with the fixation devices 14 of the present invention to increase purchase size and distribute fixation forces. Thus, such accessories may provide benefits similar to increasing the width and/or length of the distal elements. Thus, such accessories may be used with fixation devices of fixed dimension or with fixation devices having distal elements of varying dimension.

FIGS. 17A-17B illustrate an embodiment of an accessory 150. In this embodiment, the accessory 150 comprises a support 152 which is positioned to support the tissue which is being grasped by the fixation device 14. FIG. 17A illustrates valve leaflets LF being grasped by a fixation device 14. The fixation device 14 includes a pair of distal elements 18 which are joined with a coupling member 19 and moveable between at least an open and closed position by a pair of legs 68. In this embodiment, engagement surfaces 50 of the distal elements 18 contact the downstream surfaces of the leaflets LF. In this embodiment, the support 152 has at least two planar sections, each planar section configured to mate with an engagement surface of a distal element 18 when coupled. Typically, the fixation device 14 is released from a delivery catheter, yet maintained by a tether 154, to determine if regurgitation has been sufficiently reduced. If additional support is desired, the support 152 is advanced down the tether 154, as depicted in FIG. 17A, and positioned against the upstream surfaces of the leaflets, as depicted in FIG. 17B. The support 152 is then attached to the fixation device 14 and the tether 154 removed.

7. Combinations. Any of the above described features and accessories may be present in any combination in a fixation device of the present invention. For example, a fixation device 14 may have distal elements 18 that vary in width and in length, either simultaneously or independently. Or, the fixation device may have distal elements 18 that are splayable and vary in length or width or length and width, all of which may occur simultaneously or independently. Or, in another example, the fixation device 14 may have one distal element 18 which is longer than the other wherein one or both distal elements 18 vary in width. Further, mechanisms related to each feature may be present in any combination. For example, a fixation device 14 may have one distal element 18 that varies in width by action of a flap 104 and another distal element 18 that varies in width by action of a pontoon 108. Still further, a fixation device 14 may include some distal elements 18 which have one or more of the above described features and some distal elements 18 which do not.

FIGS. 18A-18B illustrate an embodiment of a fixation device 14 combining the features presented in FIGS. 8A-8B and FIGS. 13A-13B. In this embodiment, each distal element 18 has one or more loops 100 which are extendable laterally outward in a direction perpendicular to longitudinal axis 66 and extendable outward along longitudinal axis 66. FIG. 18A illustrates the loops 100 in a retracted position, wherein the distal elements 18 each have a width and length substantially determined by the size of the distal element 18 itself. In this embodiment, some of the loops 100 are disposed on a surface of the distal elements 18 opposite the engagement surfaces 50 when in the retracted position. However, it may be appreciated that the loops 100 may be disposed on the engagement surfaces 50 or within the distal elements 18 themselves. FIG. 18B illustrates the loops 100 in an expanded position wherein the loops 100 extend laterally outward in a direction perpendicular to longitudinal axis 66 and outward along longitudinal axis 66. Expansion may be active or passive. The loops 100 may be comprised of any suitable material including wire, polymer, shape-memory alloy, Nitinol™, suture, or fiber, to name a few. Further, it may be appreciated that any number of loops 100 may be present and the loops 100 may extend any distance.

Figures 19A, 19B, 19C:
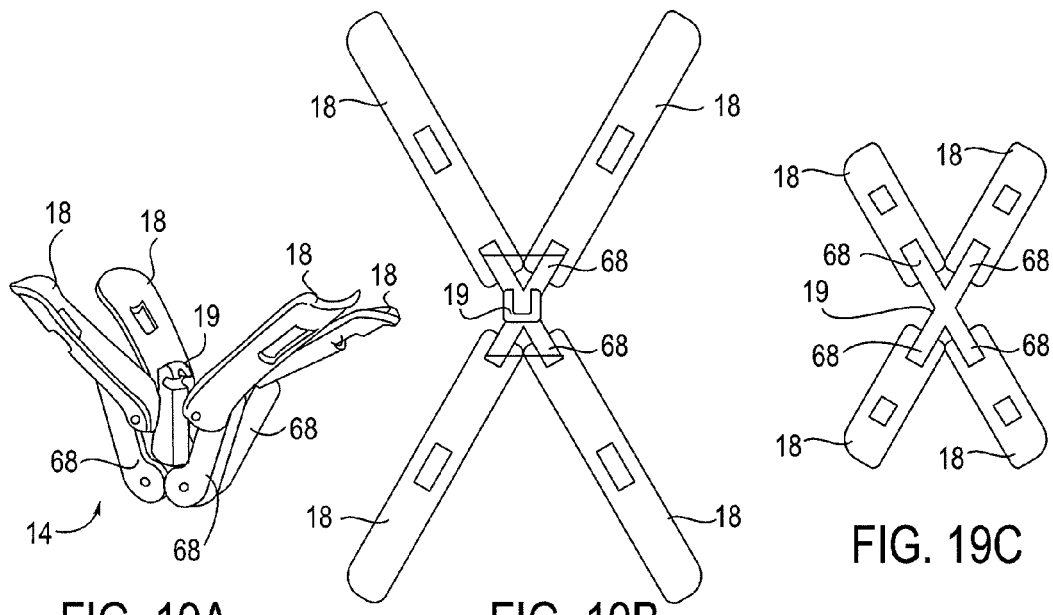
FIGS. 19A-19C, 20A-20C illustrate embodiments of a fixation device combining splaying and variable length distal elements.

FIGS. 19A-19C illustrate an embodiment of a fixation device 14 combining splaying and variable length distal elements. FIG. 19A provides a perspective view of a fixation device 14 having four distal elements 18. Each distal element 18 is connected with a coupling member 19 and a leg 68, wherein actuation of the legs 68 move the distal elements 18 between at least an open and closed position. FIG. 19B provides a top view of the fixation device 14 of FIG. 19A in the open position illustrating the splaying of the distal elements 18. In this embodiment, the distal elements 18 are fixed in a splayed position. When in the open position, the fixation device 14 can be positioned to grasp tissue, such as a valve leaflet. Transitioning to a closed position retracts the distal elements 18 as illustrated in FIG. 19C. Similarly, as mentioned above, tissue may be captured or "pinched" between the distal elements 18. Further, retraction of the distal elements may drag the tissue inwardly. Together, such actions may assist in gathering up the leaflet to tighten the plication while also providing a more secure grasp on the captured tissue.

Figures 20A, 20B, 20C:
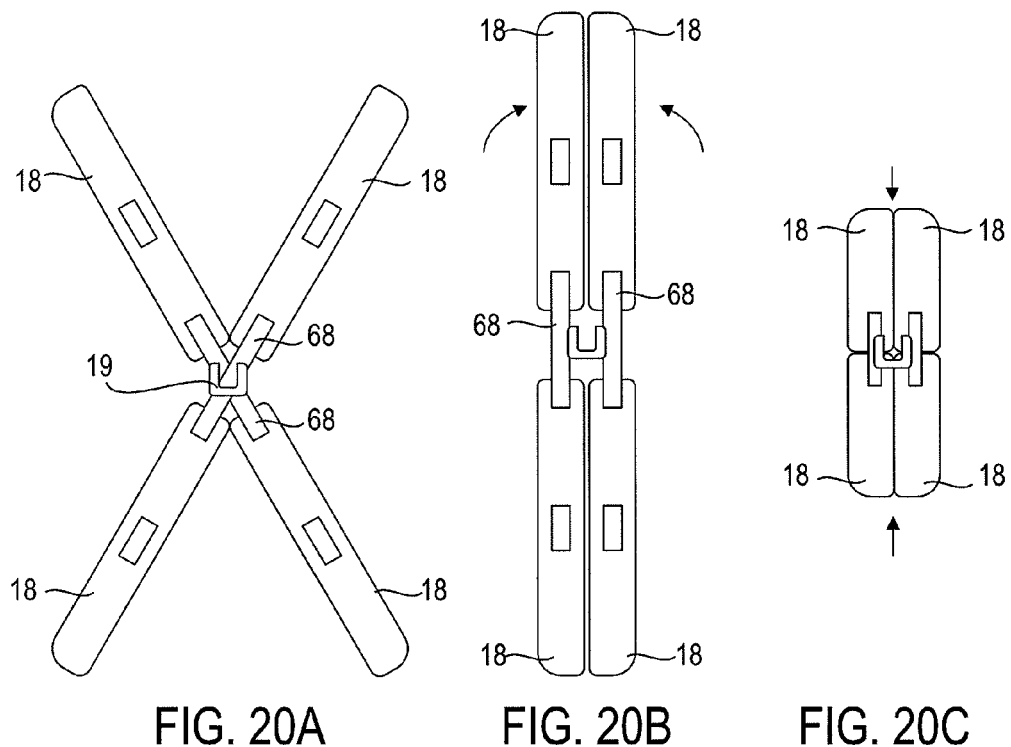

FIGS. 20A-20C also illustrates an embodiment of a fixation device 14 combining splaying and variable length distal elements. FIG. 20A provides a top view of the fixation device 14 having four distal elements 18. Again, each distal element 18 is connected with a coupling member 19 and a leg 68, wherein actuation of the legs 68 move the distal elements 18 between at least an open and closed position. In FIG. 20A, the distal elements 18 are shown in a splayed arrangement. However, in this embodiment, the distal elements 18 are not fixed in the splayed arrangement. FIG. 20B illustrates the distal elements 18 rotating to a parallel arrangement. Thus, when in the open position, the distal elements 18 can move between a parallel arrangement and a splayed arrangement prior to grasping tissue. Transitioning to a closed position retracts the distal elements 18 as illustrated in FIG. 20C.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A fixation device for engaging tissue, said device comprising:

at least two distal elements each having a first end, a free end opposite the first end, an engagement surface therebetween for engaging the tissue, and a longitudinal axis extending between the first end and the free end, the first ends of the two or more distal elements being movably coupled together such that the at least two distal elements are movable to engage tissue with the engagement surfaces, wherein the engagement surface comprises a concave shape for receiving the tissue; and an actuatable feature coupled to at least one of the at least two distal elements, wherein actuation of the feature varies a dimension of the at least one of the at least two distal elements which varies the size of its engagement surface.

2. The device of claim 1, further comprising two or more proximal elements, wherein each of the two or more proximal elements are at least partially recessed in the corresponding concave engagement surface of a distal element.

3. The device of claim 1, wherein each of the at least two distal elements has a width transverse to its longitudinal axis, and wherein the actuatable feature is configured so that actuation varies its width.

4. The device of claim 3, wherein the actuatable feature comprises at least one loop which is extendable laterally outwardly in a direction transverse to the longitudinal axis.

5. The device of claim 3, wherein the actuatable feature comprises at least one flap which is extendable laterally outwardly in a direction transverse to the longitudinal axis.

6. The device of claim 3, wherein the actuatable feature comprises at least one pontoon which is expandable laterally outwardly in a direction transverse to the longitudinal axis.

7. The device of claim 6, wherein the pontoon is expanded by inflation.

8. The device of claim 1, wherein each of the at least two distal elements has a length along its longitudinal axis, and wherein the actuatable feature is configured so that actuation varies its length.

9. The device of claim 8, wherein the actuatable feature comprises at least one loop which is extendable outwardly from its free end along its longitudinal axis.

10. The device of claim 8, wherein each of the at least two distal elements comprises an elongate arm, and wherein the actuatable feature comprises an extension arm coupled with the elongate arm.

11. The device of claim 10, wherein the extension arm is coupled with the elongate arm by a cam such that rotation of the cam advances the extension arm along the longitudinal axis.

12. The device of claim 10, wherein each distal element is moveable from a closed position wherein the engagement surfaces of the at least two distal elements are closer together to an open position wherein the engagement surfaces of the at least two distal elements are further apart, and wherein movement between the closed and open position advances the extension arm of each distal element along its longitudinal axis.

13. The device of claim 1, wherein each of the at least two distal elements has a width transverse to its longitudinal axis and a length along its longitudinal axis, and wherein the actuatable feature is configured so that actuation varies its width and length.

14. The device of claim 1, wherein the at least two distal elements are in an opposed orientation so that the engagement surfaces face one another such that the tissue is captured therebetween.

15. The device of claim 1, wherein the at least two distal elements are alignable so that the corresponding longitudinal axes are substantially parallel with one another.

\* \* \* \* \*